United States Patent [19]

Feild

[11] 4,013,078
[45] Mar. 22, 1977

[54] INTERVERTEBRAL PROTECTOR MEANS

[76] Inventor: James R. Feild, 2254 N. Parkway, Memphis, Tenn. 38112

[22] Filed: Oct. 7, 1975

[21] Appl. No.: 620,419

Related U.S. Application Data

[63] Continuation-in-part of Ser. No. 526,686, Nov. 25, 1974, abandoned, which is a continuation-in-part of Ser. No. 518,523, Oct. 29, 1974, abandoned.

[52] U.S. Cl. .......................................... 128/303 R
[51] Int. Cl.² ........................................ A61B 19/00
[58] Field of Search .................... 128/303 R, 132 R

[56] References Cited

UNITED STATES PATENTS

| 2,127,903 | 8/1938 | Bowen | 128/334 R |
| 3,014,483 | 12/1961 | McCarthy | 128/132 R X |
| 3,823,705 | 7/1974 | Trimble | 128/1 R |
| 3,833,002 | 9/1974 | Palma | 128/334 R |

FOREIGN PATENTS OR APPLICATIONS 615,861  1/1949  United Kingdom ............... 128/132

OTHER PUBLICATIONS

McNealy Viscera Retainer SU-15800, IN "Guide To Purchasing, 1956," publication of V. Mueller & Co., Chicago.

Primary Examiner—Channing L. Pace
Attorney, Agent, or Firm—John R. Walker, III

[57] ABSTRACT

A protective device for preventing the development of postoperative adhesions between a patient's dura and spinal nerves and other anatomic structures after spinal surgery. Preferably, the protective device provides an intervening barrier between portions of the patient's dura and spinal nerves in the patient's spinal canal following intervertebral disc surgery in which a portion of one of the patient's intervertebral discs and a portion of the patient's vertebra adjacent the disc are removed.

28 Claims, 23 Drawing Figures

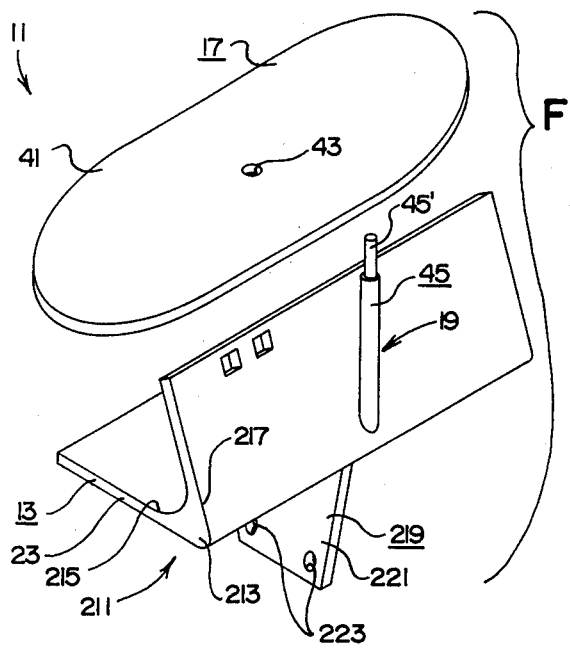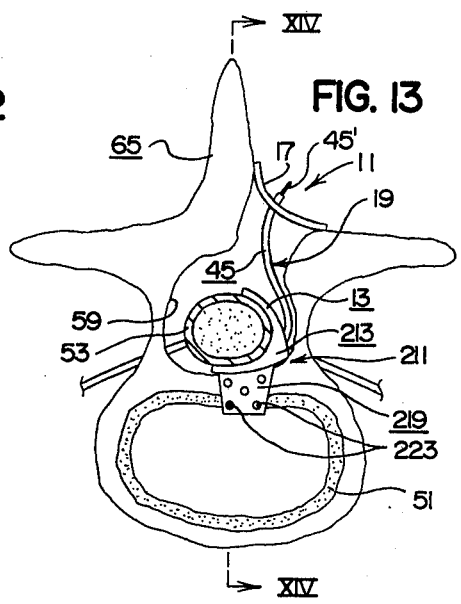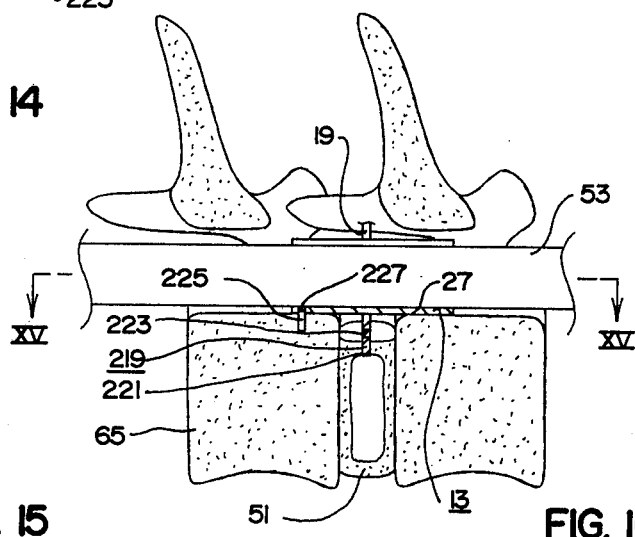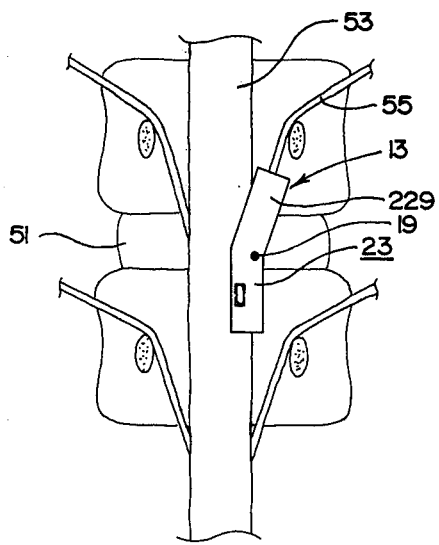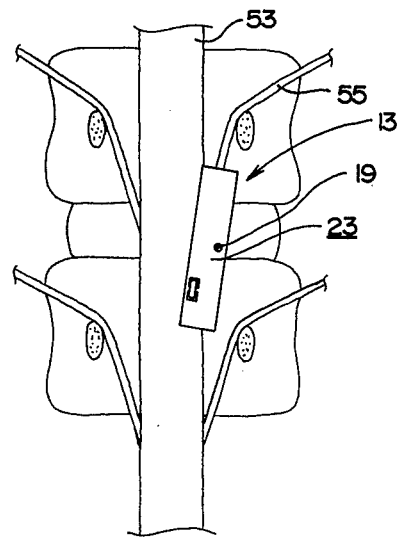

INTERVERTEBRAL PROTECTOR MEANS

CROSS-REFERENCE TO RELATED APPLICATION

This is a continuation-in-part of my application, Ser. No. 526,686, filed Nov. 25, 1974, now abandoned which was a continuation-in-part of my application, Ser. No. 518,523, filed Oct. 29, 1974 now abandoned.

BACKGROUND OF THE INVENTION

This invention relates generally to medical devices and more specifically to means for protecting a patient's dura and spinal nerves and other spinal canal structure following intervertebral and intravertebral spinal surgery to prevent the development of postoperative adhesions therebetween.

Following intervertebral surgery such as the removal of portions of a ruptured or herniated intervertebral disc, adhesions and scar tissue develop in the spinal canal between the dura, spinal nerves, vertebral body and the space where the portion of the disc was removed. Such adhesions and scar tissue often bind the unprotected spinal nerve causing substantial pain and in some instances requiring another operation to free the spinal nerve with the hope that when the incision made to free the spinal nerve heals the spinal nerve will not be again bound by adhesions and scar tissue. In addition, when another operation is required, the adhesions and scar tissue further complicate matters by obstructing the surgeon's view of the affected area. More importantly, when the surgeon attempts to remove the adhesions and scar tissue from the affected area, the dura is often reptured due to the strong bond that develops between the adhesions and scar tissue and the dura.

SUMMARY OF THE INVENTION

The present invention is directed towards preventing the development of adhesions and scar tissue between a patient's dura and spinal nerves and other spinal canal structures following spinal surgery to preclude subsequent binding of the spinal nerves. The concept of the present invention is to provide an intervening barrier between portions of the patient's dura and spinal nerves and the patient's spinal canal adjacent the surgical site with a biocompatible protector means thereby preventing the development of postoperative adhesions between the patient's dura and spinal nerves and certain other spinal canal structures.

The protector means of the present invention is specifically adapted for use following intervertebral surgery to remove a portion of a ruptured or herniated intervertebral lumbar disc and preferably includes shield means for providing an intervening barrier between a portion of the patient's dura and the patient's spinal canal adjacent the partially removed portion of the disc to prevent development of postoperative adhesions on the patient's dura between the partially removed disc and the dura. Additonally, the shield means may provide an intervening barrier between a portion of the patient's spinal nerve and the patient's spinal canal adjacent the partially removed portion of the disc to prevent development of postoperative adhesions therebetween. The protector means may also include a conduit means for covering a portion of the spinal nerve adjacent the removed portion of the disc to prevent development of postoperative adhesions therebetween. Also, since it is the typical procedure to remove a portion of the patient's vertebrae adjacent the disc, the present invention may include roof means for covering the removed portion of the vertebrae to obstruct passage of blood and the like therethrough.

BRIEF DESCRIPTION OF THE DRAWINGS

FIG. 12 is a perspective view of the intervertebral protector means of the present invention showing a modified form of the shield means thereof.

FIG. 13 is an end elevational view of the intervertebral protector means of the present invention shown in FIG. 12 with the intervertebral protector means inserted in a patient.

FIG. 14 is a sectional view of the present invention as taken on line XIV—XIV of FIG. 13.

FIG. 15 is a sectional view of the present invention as taken on line XV—XV of FIG. 14.

FIG. 16 is a sectional view of the present invention similar to FIG. 15 but showing a modified form of the shield means of the present invention.

DESCRIPTION OF THE PREFERRED EMBODIMENT

Figure 1:
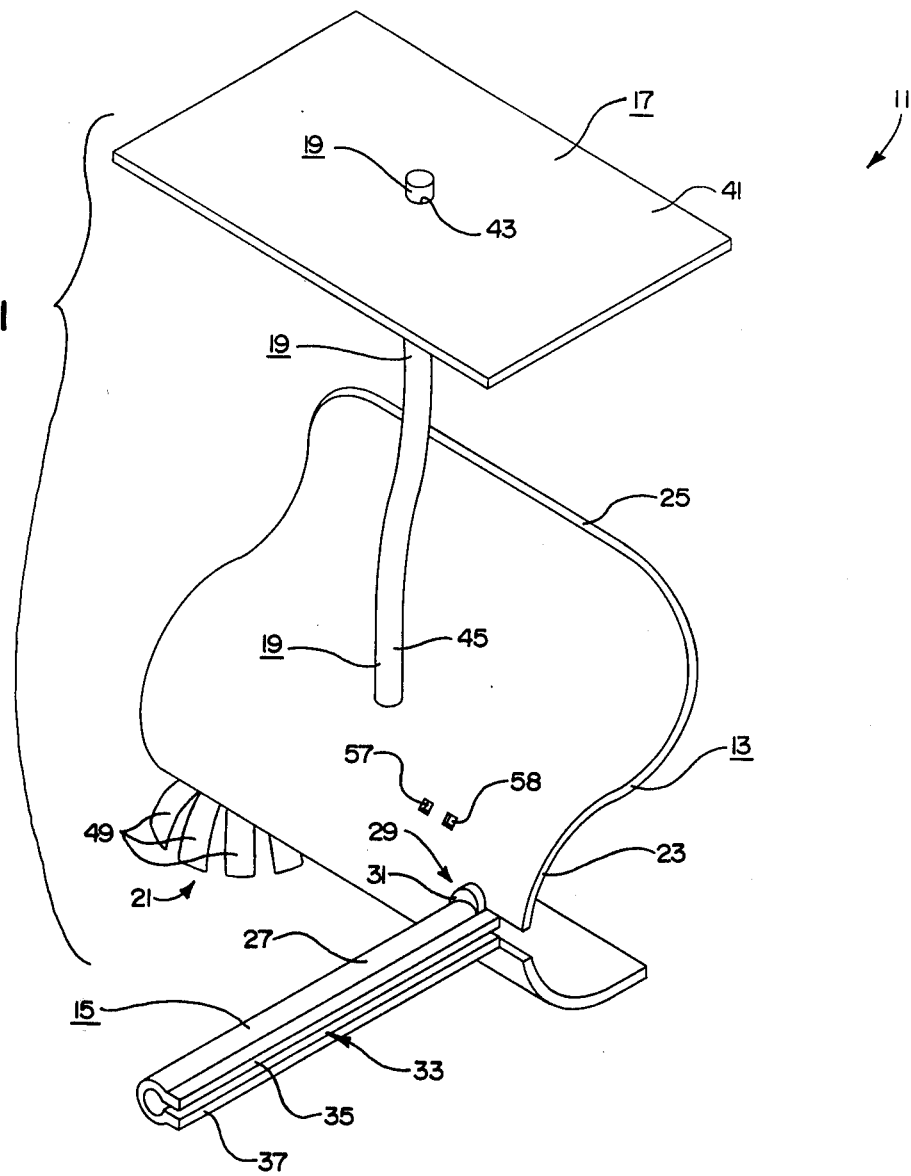
FIG. 1 is a perspective view of the intervertebral protector means of the present invention.
Figure 2:
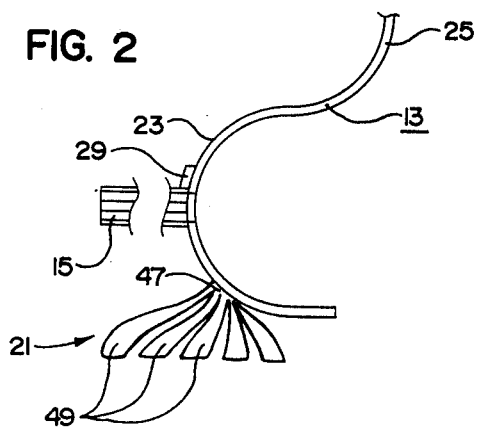
FIG. 2 is an end elevational view of the intervertebral protector means of the present invention with some parts removed for clarity.
Figure 3:
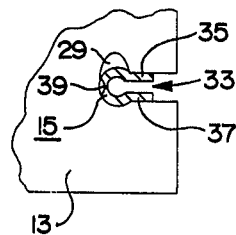
FIG. 3 is a side elevational view of a portion of the intervertebral protector means of the present invention with some parts thereof removed for clarity.

The intervertebral protector means 11 of the present invention is for use following intervertebral and intravertebral spinal surgery to prevent the development of postoperative adhesions between the patient's dura and spinal nerves and the partially removed intervertebral disc and vertebrae and is specifically adpated for use following intervertebral disc surgery in which a portion of a ruptured or herniated intervertebral lumbar disc is removed. When an intervertebral disc ruptures, it usually pinches the spinal nerve emerging from the spinal cord at a location adjacent the ruptured disc causing substantial pain and typically requiring surgery to remove the ruptured portion of the disc. The usual method of removing a portion of a ruptured disc is to first make an incision in the middle of the patient's back adjacent the spinal processes of the verterbrae adjacent the ruptured disc. Next, the muscle and flesh adjacent the vertebrae are pulled back, giving the surgeon access to the lamina and adjacent vertebral structure. The surgeon then removes part of the lamina and, perhaps, part of the adjacent vertebral structure to permit entry into the spinal canal of the vertebra adjacent the ruptured disc. Access to a portion of the ruptured disc is had adjacent the cauda equina and the dura covering the cauda equina in the spinal canal. A small aperture is made in the section of the ruptured disc accessible by the surgeon and a portion of the disc is removed in a manner well known to those skilled in the art. The protector means 11 is adapted to provide an intervening barrier between portions of the patient's dura and spinal nerve and the patient's spinal canal adjacent the surgical site to prevent development of postoperative adhesions between the patient's dura and the spinal nerves and the partially removed disc and adjacent structures in the spinal canal.

The protector means 11 of the present invention preferably includes a shield means 13 for providing an intervening barrier between a portion of the patient's dura and the patient's spinal canal adjacent the removed portion of the disc to prevent development of postoperative adhesions between the patient's dura and the partially removed disc. Additionally, the shield means 13 may be adapted to provide an intervening barrier between a portion of the patient's spinal nerve emerging from the cauda equina and dura at a location adjacent the removed portion of the disc and the patient's spinal canal to prevent development of postoperative adhesions between the patient's spinal nerve and partially removed disc and adjacent structures in the spinal canal. The protector means 11 may include conduit means 15 for covering a portion of the spinal nerve emerging from the cauda equina and dura at a location adjacent the removed portion of the disc to prevent development of postoperative adhesions therebetween. In addition, the protector means 11 may include roof means 17 for covering the removed portion of the vertebra to obstruct passage therethrough and may include joining means 19 for joining the roof means 17 to the shield means 13. Furthermore, the protector means 11 may include filler means 21 for occupying any vacant space in the spinal canal adjacent the removed portion of the disc to prevent development of postoperative adhesions therein.

Figure 18:
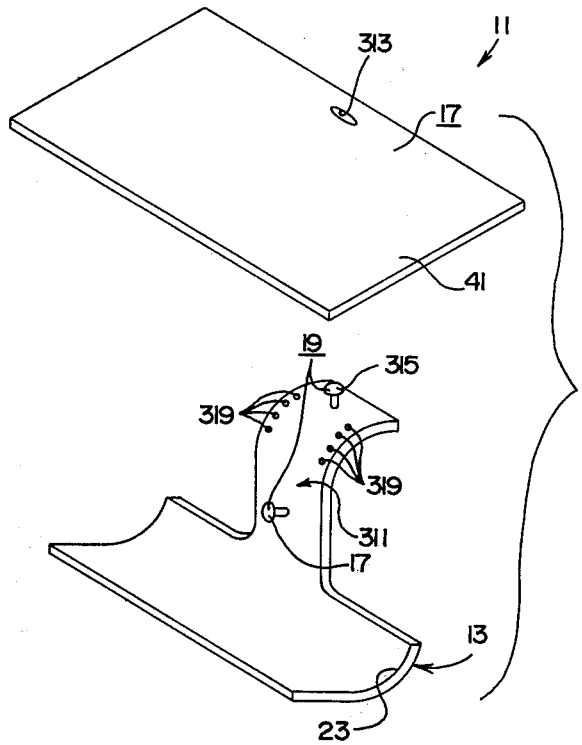
FIG. 18 is a perspective view of the intervertebral protector means of the present invention showing a modified form of the shield means and roof means thereof.
Figure 19:
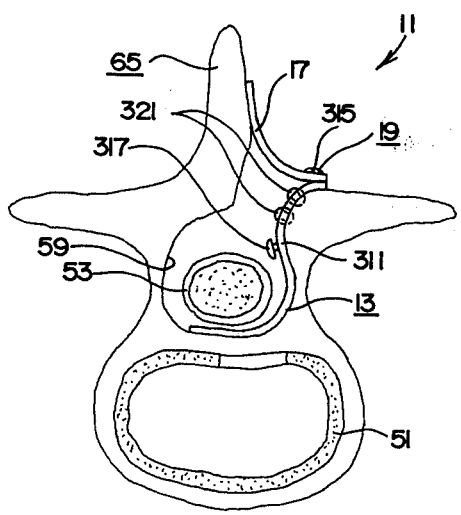
FIG. 19 is an end elevational view of the intervertebral protector means shown in FIG. 18 with the intervertebral protector means inserted in a patient.
Figure 20:
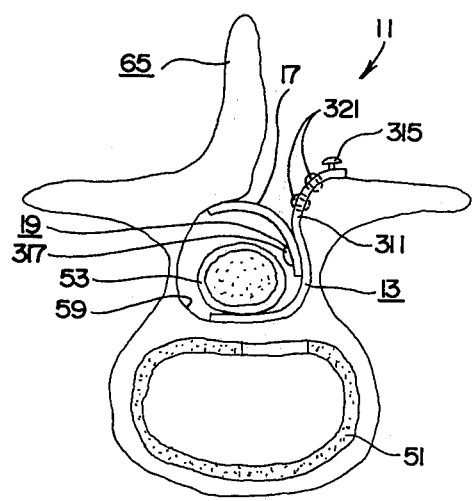
FIG. 20 is an end elevational view of the intervertebral protector means similar to FIG. 19 but showing the intervertebral protector means inserted in the patient in a different manner from that shown in FIG. 19.

The shield means 13 preferably includes a semi-cylindrical body portion 23 for extending around a portion of the dura adjacent the removed portion of the disc to prevent development of postoperative adhesions therebetween. The shield means 13 may also include a tongue portion 25 integrally joined to the body portion 23 for extending between the dura and the removed portion of the vertebra to obstruct passage therebetween. The tongue portion 25 of the shield means 13 may include a backwardly curving portion 311 to give the shield means 13 a substantially "S" cross-sectional shape as shown in FIGS. 18, 19 and 20. This backwardly curving portion 311 allows the shield means to be anchored to the patient's spine in a manner which will hereinafter become apparent. The shield means 13 is preferably composed of a biocompatible synthetic plastic such as silicone. The shield means 13 may include ribs (not shown) for stability.

The conduit means 15 preferably includes a tubular body portion 27 for completely enveloping the portion of the spinal nerve emerging from the dura adjacent the removed portion of the disc to prevent development of postoperative adhesions therebetween. Also, the conduit means 15 preferably includes a head portion 29 for joining the body portion 27 of the conduit means 15 to the body portion 23 of the shield means 13. The head portion 29 may be attachable to the body portion 23 of the shield means 13 in any number of ways. For example, the head portion 29 may include a rim portion 31 positioned transverse to the body portion 27 of the conduit means 15 for attachment to the body portion 23 of the shield means 13 by sutures or the like. In addition, it should be noted that the head portion 29 may be integrally attached to the body portion 23 of the shield means 13. That is, the shield means 13 and the conduit means 15 may be a one-piece unit. The body portion 27 of the conduit means 15 includes a longitudinal groove 33 for allowing the body portion 27 to be inserted around the spinal nerve. Preferably the body portion 27 of the conduit means 15 includes a first longitudinal flange member 35 adjacent the first side of the longitudinal groove 33 and includes a second longitudinal flange member 37 adjacent the second side of the longitudinal groove 33. The first and second longitudinal flange members 35, 37 are positioned adjacent one another and are adapted to be joined to one another after the body portion 27 of the conduit means 15 is inserted around the spinal nerve. More specifically, the first and second longitudinal flange members 35, 37 may be joined to one another by sutures, by clamps, by glue or by melting. When the body portion 27 is constructed of a suitable friction-free, biocompatible material such as Teflon, silicone, or the like, friction between the spinal nerve and the walls of the body portion 27 will be negligible. The body portion 27 of the conduit means 15 is adapted to be bent to follow the normal angulation of the spinal nerve. More specifically, the body portion 27 may include a window-like portion 39 in which the wall of the body portion 27 is substantially thinner than the rest of the body portion 27 to allow the body portion 27 to be easily bent to follow the angulation of the spinal nerve. In addition, the body portion 27 of the conduit means 15 may include an enlarged portion (not shown) to accommodate any ganglionic enlargement of the spinal nerve.

The roof means 17 preferably includes a sheet 41 for placement above the lamina outside the spinal canal to prevent the muscles and flesh adjacent the vertebra from bleeding into the spinal canal and giving rise to adhesions. The sheet 41 may include an aperture 43 thereof (see FIGS. 1 and 12) for attachment to the joining means 19. On the other hand, the sheet 41 may include a buttonhole-like aperture 313 at one edge thereof (see FIG. 19) for attachment to the joining means 19 in a manner which will hereinafter become apparent. Furthermore, the sheet 41 may include a slit-like aperture 411 at one edge thereof (see FIG. 21) for attachment to the joining means 19 in a manner which will hereinafter become apparent. The sheet 41 may be rectangular shaped (see FIG. 1), oval shaped, or the like. The sheet 41 is preferably constructed of a biocompatible synthetic material well known to those skilled in the art.

Figure 21:
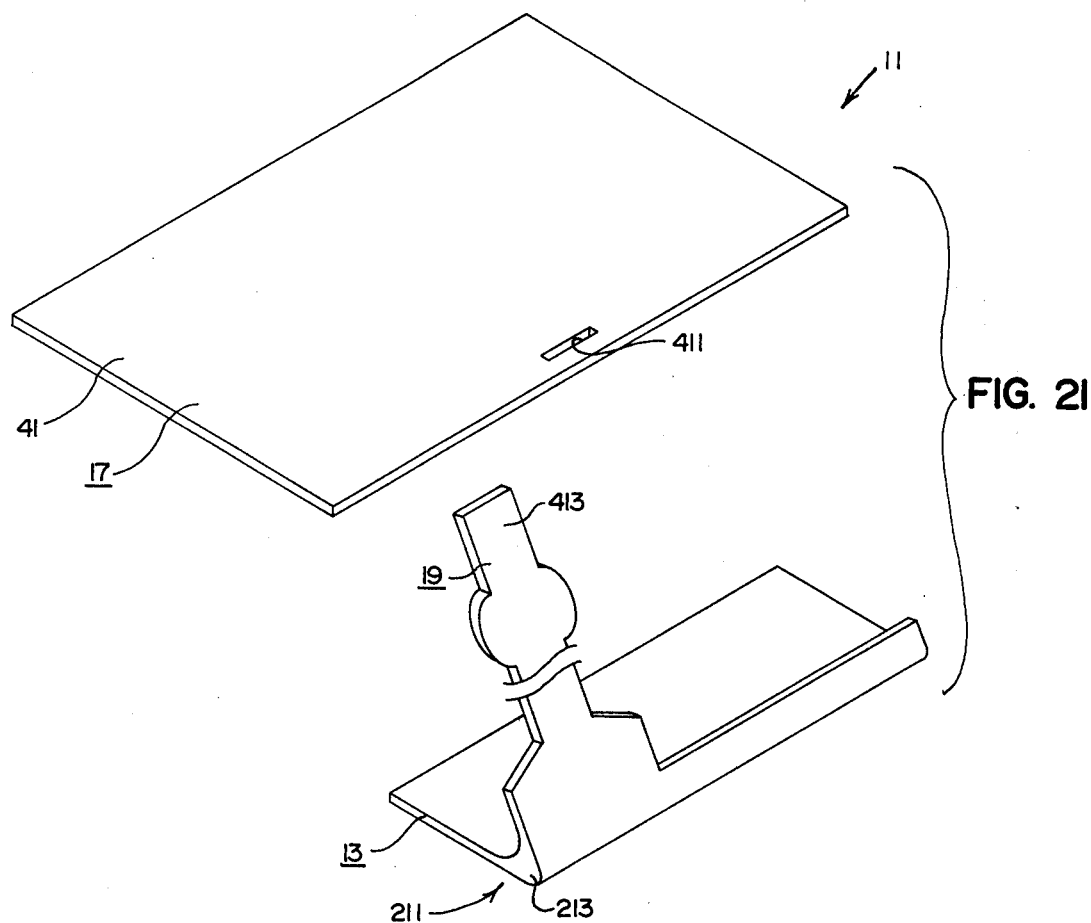
FIG. 21 is a perspective view of the intervertebral protector means of the present invention showing a modified form of the shield means and roof means thereof.
Figure 22:
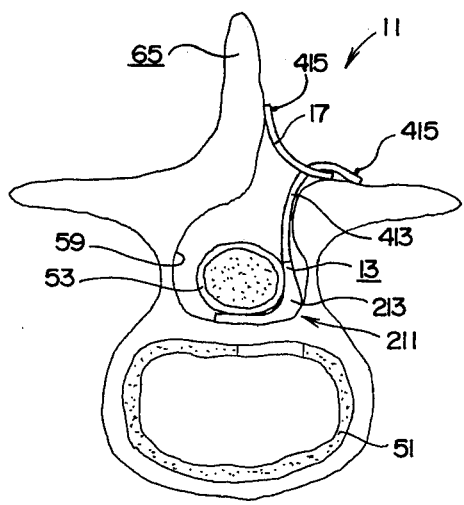
FIG. 22 is an end elevational view of the intervertebral protector means shown in FIG. 21 with the intervertebral protector means inserted in a patient.
Figure 23:
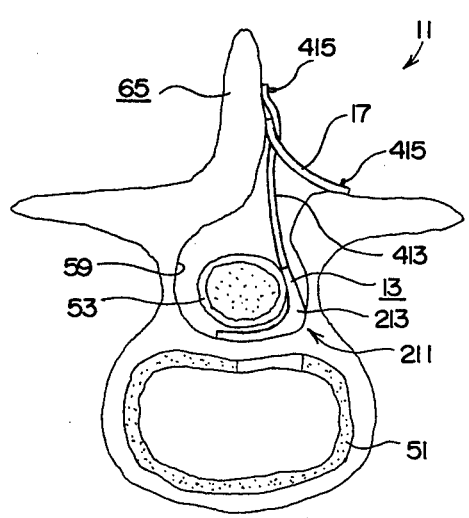
FIG. 23 is an end elevational view of the intervertebral protector means similar to FIG. 22 but showing the intervertebral protector means inserted in the patient in a different manner from that shown in FIG. 22.

The joining means 19 may include a rodlike projection 45 fixedly attached at one end to the body portion 23 of the shield means 13 and extending upwardly therefrom. The other end of the rodlike projection 45 is adapted to fit into the aperture 43 and the sheet 41. The sheet 41 is adapted to be secured to the rodlike projection 45 in any number of ways. For example, the sheet 41 may be sutured to the rodlike projection 45. Also, the rodlike projecton 45 may be of a cross-sectional size larger than the aperture 43 in the sheet 41 so that once the rodlike projection 45 has been inserted into the aperture 43 in the sheet 41, friction between the rodlike projection 45 and the walls of the aperture 43 will anchor the rodlike projection 45 and the sheet 41 together. The rodlike projection 45 is preferably provided with a portion 45' of reduced cross-sectional size (see FIGS. 12 and 13) for aiding the insertion of the rodlike projection 45 into the aperture 43. That is, the portion 45' is adapted to be easily inserted through the aperture 43 whereupon force may be applied to the portion 45' to stretch the projection 45 to a narrower diameter and pull the rodlike projection 45 through the aperture 43 thereby allowing the rodlike projection 45 and the sheet 41 to be anchored together. On the other hand, the joining means 19 may include a first button-like member 315 and/or a second button-like member 317 attached to the shield means 13 as shown in FIGS. 18, 19 and 20 and adapted to coact with the buttonhole-like aperture 313 of the sheet 41 for joining the sheet 41 and the shield means 13. More specifically, the first button-like member 315 is preferably attached to the backwardly curving portion 311 of the tongue portion 25 of the shield means 13 as shown in FIG. 18 to allow the sheet 41 of the roof means 17 to be positioned along the outside surface of the patient's vertebra as shown in FIG. 19. The second button-like member 317 is preferably attached to the shield means 13 intermediate the body portion 23 and the tongue portion 25 to allow the sheet 41 of the roof means 17 to be positioned along the inside surface of the patient's spinal canal as shown in FIG. 20. On the other hand, the joining means 19 may include an arm member 413 fixedly attached to the shield means 13 as shown in FIGS. 21, 22 and 23 and adapted to coact with the slit-like aperture 411 of the sheet 41 for joining the sheet 41 and the shield means 13 together. FIGS. 22 and 23 show two methods by which the slit-like aperture 411 and the arm member 413 may be used to join the sheet 41 and the shield means 13 together. In FIG. 22, the arm member 413 extends substantially straight upwards along the removed portion of the vertebra and through the slit-like aperture 411 in the sheet 41. In FIG. 23, the arm member 413 extends across the removed portion of the vertebra and through the slit-like aperture 411 in the sheet 41. It should be noted that when the sheet 41 and the shield means 13 are joined together as shown in FIG. 23, the sheet 41 is turned 180° about a vertical axis from its position as shown in FIG. 21.

The filler means 21 preferably includes a base member 47 and a plurality of finger members 49 extending outwardly from the base member 47. The base member 47 is adapted to be securely attached to the body portion 23 of the shield means 13 by any number of ways. For example, the base member 47 of the filler means 21 may be sutured to the body portion 23 of the shield means 13. The plurality of finger members 49 coact together to form a substantially globe-shaped body which can be easily cut to shape by the surgeon to occupy any vacant space in the spinal canal adjacent the removed portion of the disc to prevent development of postoperative adhesions and scar tissue therein. The filler means 21 specifically prevent the development of postoperative adhesions on the spinal nerve that exists the spinal canal through the intervertebral foramen adjacent the removed portion of the disc. It should be noted that the spinal nerve that exits the intervertebral foramen adjacent the removed portion of the disc emerges from the dura adjacent the disc just above the disc that had a portion thereof removed.

Figure 4:
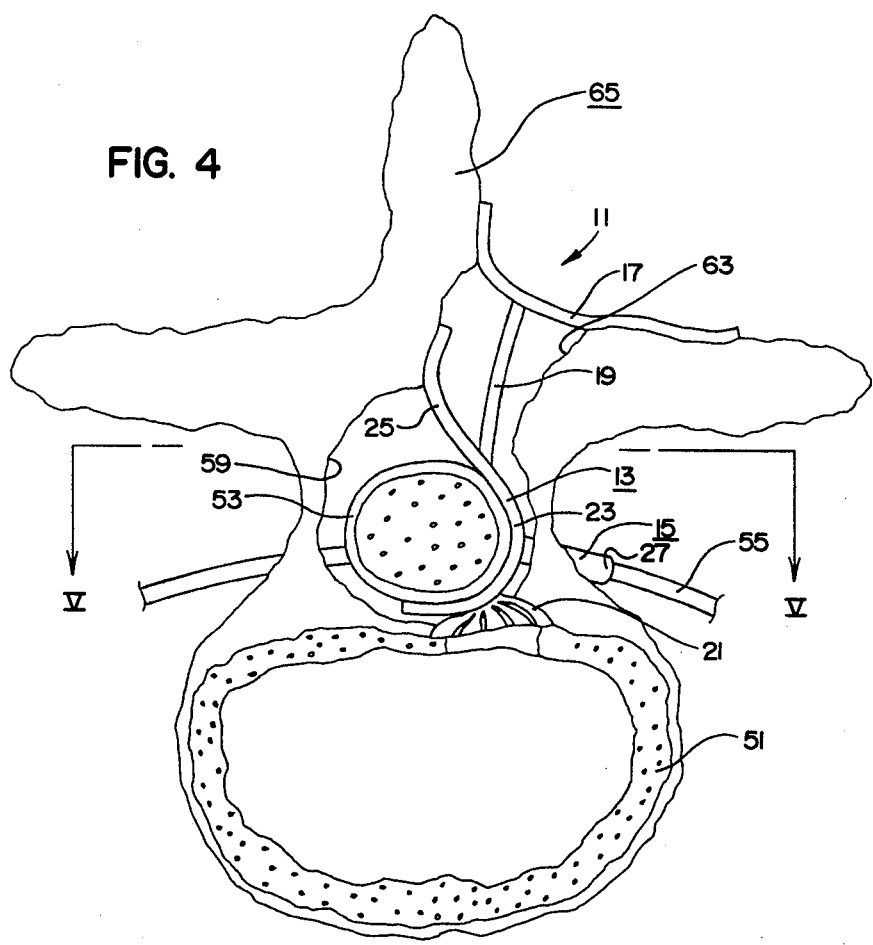
FIG. 4 is an end elevational view of the intervertebral protector means of the present invention shown inserted in a patient.
Figure 5:
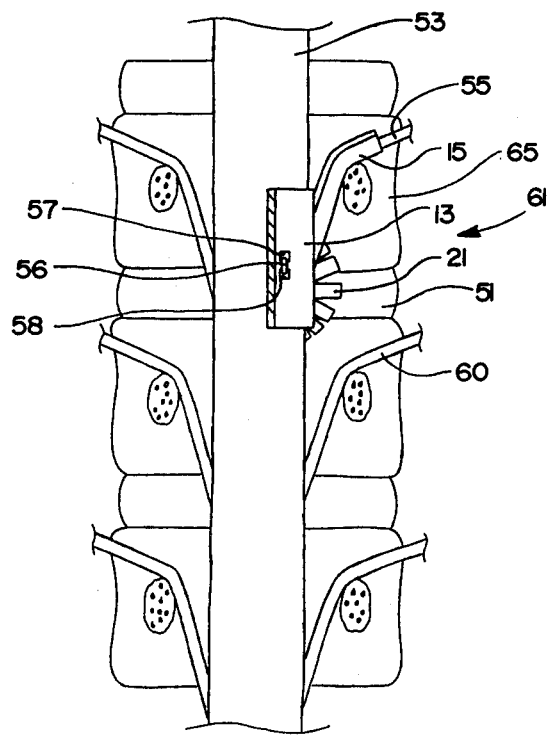
FIG. 5 is a sectional view of the present invention as taken on line V—V of FIG. 4 shown inserted in a patient.

Referring particularly to FIGS. 4 and 5 of the drawings, the insertion and use of the protector means 11 will now be explained with specific reference to various parts of the anatomy. First, after the disc 51 is partially removed by well-known methods to correct a rupture or the like therein, the body portion 23 of the shield means 13 is inserted around the dura 53 and the body portion 27 of the conduit means 15 is inserted over the spinal nerve 55 which emerges from the dura 53 adjacent the removed portion of the disc 51. After the body portion 27 of the conduit means 15 is inserted over the spinal nerve 55, the head portion 29 of the conduit means 15 is fixedly attached to the body portion 23 of the shield means 13 as by sutures (not shown) and the first and second longitudinal flange members 35, 37 of the body portion of the conduit means 15 are fixedly attached to each other as by sutures or otherwise. The body portion 23 may be fixedly attached to the dura 53 by sutures 56 (see FIG. 5). More specifically, the body portion 23 of the shield means 13 may be provided with a first window or aperture 57 and a second window or aperture 58 for allowing passage of the sutures 56 therethrough to attach the body portion 23 to the dura 53. The filler means 21 is then placed over the removed portion of the disc 51 and the plurality of finger members 49 of the filler means 21 are cut to allow the filler means 21 to occupy any vacant space in the spinal canal 59 adjacent the removed portion of the disc 51 and the spinal nerve 50 which exits the spinal canal 59 through the intervertebral foramen 61 adjacent the removed portion of the disc 51. The base member 47 of the filler means 21 is then fixedly attached to the body portion 23 of the shield means 13 as by sutures (not shown) or the like. Next, the sheet 41 of the roof means 17 is placed over the removed portion of the lamina 63 of the spinal vertebra 65, cut to size, and attached to the rodlike projection 45 of the joining means 19 as by sutures (not shown) or the like. Notches (not shown) or the like may be cut into the sheet 41 to allow the sheet 41 to fit around the spinal processes of the patient's vertebrae. Any portion of the rodlike projectin 45 that extends above the sheet 41 is preferably cut off. The insertion of the protector means 11 is then complete and the incision along the patient's back can be closed.

Figure 6:
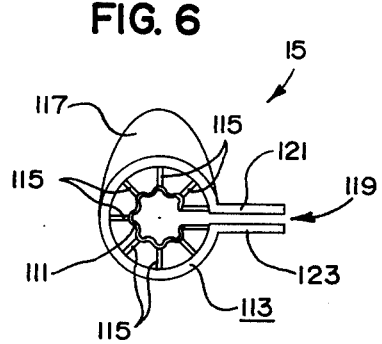
FIG. 6 is an end elevational view of a modified form of the conduit means of the present invention.
Figure 7:
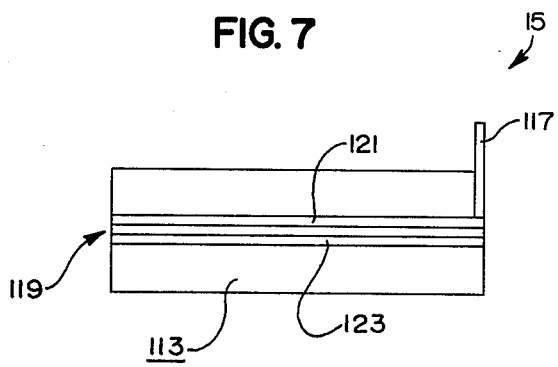
FIG. 7 is a side elevational view of the modified form of the conduit means of the present invention.

It should be noted that applicant envisions various changes and modifications to the structure of the protector means 11 in order to meet various conditions that may arise. For example, the conduit means 15 may consist of a tube-within-a-tube when it is desired to reduce to a minimum the amount of friction between the spinal nerve 55 and the conduit means 15. More specifically, the conduit means 15 may include a first tubular body portion 111 for completely enveloping the portion of spinal nerve 55 adjacent the removed portion of the disc 51, a second tubular body portion 113 for enveloping the first tubular body portion 111, and a plurality of flexible ribs 115 or the like for attaching the first tubular body 111 inside the second tubular body portion 113 (see FIGS. 6 and 7). In this manner, the first tubular body portion 111 is allowed a limited degree of substantially friction-free movement relative to the second tubular body portion 113. Thus, even if adhesions and scar tissue binds the second tubular body portion 113 after the protector means 11 has been inserted, the mount of friction between the spinal nerve 55 and the conduit means 15 is still slight. The second tubular body portion 113 may be provided with a head portion 117 for joining the conduit means 15 to the shield means 13 in the same manner as heretofore described with respect to head portion 29. Also, the first and second tubular body portions 111, 113 may include a longitudinal groove 119 and first and second flange members 121, 123 for the same reasons as heretofore discussed relative to the longitudinal groove 33 and the first and second flange members 35, 37. Reference should be made to the description of the longitudinal groove 33 and the first and second flange members 35, 37 for further clarification.

Figure 8:
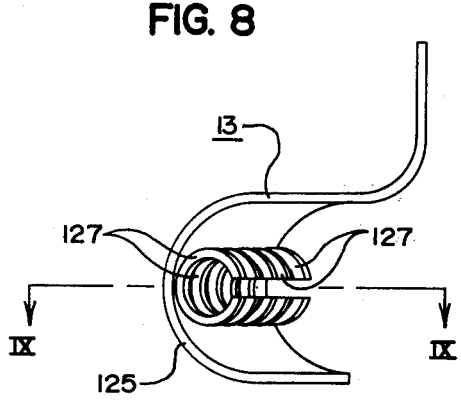
FIG. 8 is an end elevational view of a modified form of the shield means and conduit means of the present invention.
Figure 9:
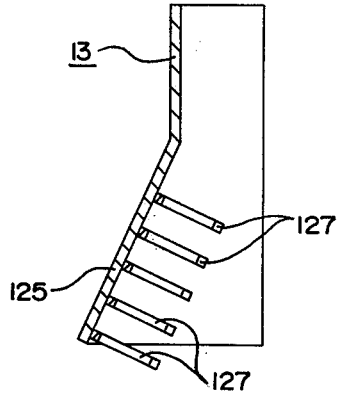
FIG. 9 is a sectional view of the modified form of the shield means and conduit means of the present invention as taken on line IX—IX of FIG. 8.

In addition, the conduit means 15 may be integrally formed with the shield means 13 when it is difficult or impossible to insert the separate components around the patient's dura 53 and spinal nerve 55. More specifically, the shield means 13 may include an offset portion 125 (see FIGS. 8 and 9) for extending around a portion of the spinal nerve 55 adjacent the dura 53 to prevent the development of postoperative adhesions thereon. Using this structure of the protector means 11, the spinal nerve 55 is covered when the shield means 13 is inserted around the dura 53 thereby doing away with the necessity of separately inserting the conduit means 15 over the spinal nerve 55. The offset portion 125 may include a plurality of grip portions 127 for holding a portion of the spinal nerve 55 to the offset portion 125.

Figure 10:
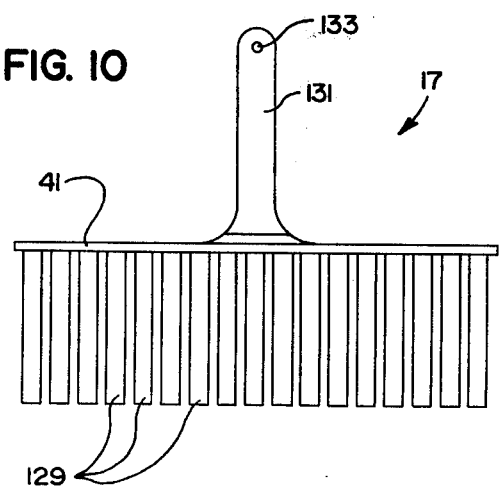
FIG. 10 is a side elevational view of a modified form of the roof means of the present invention.
Figure 11:
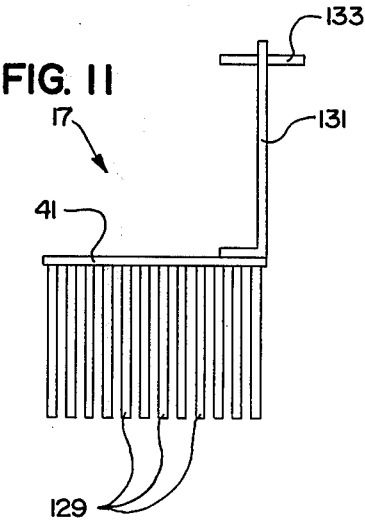
FIG. 11 is an end elevational view of the modified form of the roof means of the present invention.

The roof means 17 may include a plurality of flexible finger members 129 (see FIGS. 10 and 11) for extending from the sheet 41 of the roof means 17, through the removed portion of the lamina 63, to the shield means 13. The plurality of finger members 129 will occupy any vacant space in the removed portion of the lamina 63 between the roof means 17 and the shield means 13 to prevent the development of postoperative adhesions and scar tissue therein. It should be noted that the plurality of finger members 129 may be easily cut to properly fit the removed portion of the lamina 63.

The roof means 17 may be provided with an arm portion 131 (see FIGS. 10 and 11) for extending from the sheet 41, along the incision made into the patient's back adjacent the spinal processes of the vertebrae adjacent the ruptured disc, and stopping adjacent the patient's skin. This arm portion 131 aids subsequent reentry to the shield means 13 by a surgeon. More specifically, in the event reentry to the shield means 13 is required, the surgeon simply makes an incision into the patient's back adjacent the end of the arm portion 131 and uses the arm portion 131 as a guide to go directly to the roof means 17 and the shield means 13. A transverse marker member 133 is preferably provided on the outer end of the arm portion 131 to aid the surgeon in locating the arm portion 131. It should be noted that the arm portion 131 may be integral with the sheet 41 of the roof means 17 or may be attached thereto in any number of ways such as by sutures (not shown).

The protector means 11 may include a stabilizing means 211 to help hold the shield means 13 of the protector means 11 in place (see FIGS. 12 and 13). The stabilizing means 211 comprises a projecting member 213 preferably integrally attached to the shield means 13 on the outer side of the body portion 23 thereof. More specifically, the body portion 23 of the shield means 13 shown in FIGS. 12 and 13 includes a semi-cylindrical inner wall 215 and a substantially triangular shaped outer wall 217 with the outer portion of the substantially triangularly-shaped outer wall 217 forming the projecting member 213 of the stabilizing means 211. As can be plainly seen in FIG. 13, when the protector means 11 having the stabilizing means 211 is in place in a patient, the projecting member 213 of the stabilizing means 211 will abut against a portion of the patient's spinal canal 59 to help hold the shield means 13 of the protector means 11 in place. It should be noted that shield means 13 shown in FIGS. 12 and 13 lacks the tongue portion 25. This is because applicant envisions conditions when the tongue portion 25 may not be needed.

The protector means 11 may include a fin means 219 to help anchor the protector means 11 in place (see FIGS. 12, 13 and 14). The fin means 219 comprises a fin, platelike member 221 attached to the bottom, outer wall of the shield means 13. The platelike member 211 is located on the shield means 13 in a positon which allows the platelike member 221 to extend into the removed portion of the disc 51 when the protector means 11 is in place. The platelike member 221 of the fin means 219 is preferably provided with a plurality of apertures 223 therethrough for allowing the platelike member 211 to be firmly anchored in place by way of adhesions, scar tissue and the like growing therethrough in a manner well known to those skilled in the art.

In addition, the protector means 11 may include fastening means 225 for fastening the shield means 13 of the protector means 11 to the vertebrae 65 (see FIG. 14). The fastening means 225 may consist of a screw, nail, staple or the like for passing through an aperture 227 in the body portion 27 of the shield means 13 and into the vertebrae 65 to thereby fasten the shield means 13 to the vertebrae 65. On the other hand, the backwardly curving portion 311 of the tongue portion 25 of the shield means 13 may be provided with a plurality of apertures 319 (see FIG. 18) to allow the shield means 13 to be anchored to the patient's spine by sutures 321 or the like passing through the apertures 319 and into the patient's flesh, muscle or the like adjacent the vertebrae 65 (see FIGS. 19 and 20). Additionally, the sheet 41 and the arm member 413 of the joining means 19 may be anchored to the patient's flesh or muscle extra-durally and extra-spinally by means of sutures 415 (see FIGS. 22 and 23).

Figure 17:
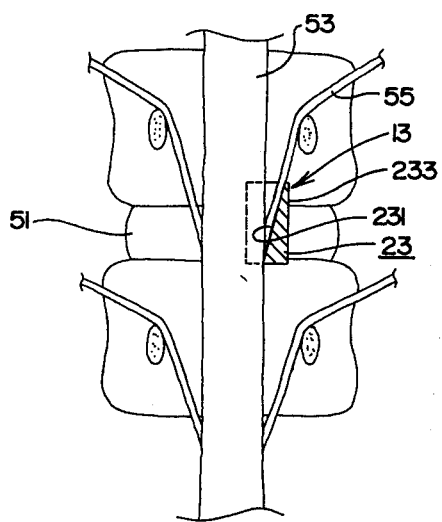
FIG. 17 is a sectional view of the present invention similar to FIGS. 15 and 16 but showing a modified form of the shield means of the present invention.

FIGS. 15, 16 and 17 show three forms of the protector means 11 in which the conduit means 15 is omitted. In FIG. 15, the body portion 23 of the shield means 13 includes an offset portion 229 to accomodate the spinal nerve 55 which emerges from the dura 53 adjacent the removed portion of the disc 51. That is, since the spinal nerves emerge from the dura 53 at or near a 15° angle, the offset portion 229 preferably emerges from the remainder of the body portion 23 at or near a 15° angle. In FIG. 16, the body portion 23 of the shield means 13 is straight. That is, the body portion 23 in FIG. 16 does not include an offset portion to accommodate the spinal nerve 55. To allow the body portion 23 in FIG. 16 to accommodate the spinal nerve 55, the body portion 23 is positioned at or near an angle of 15° to the dura 53 as clearly shown in FIG. 16. In FIG. 17, the inner wall 231 of the shield means 13 is located at or near a 15° angle relative to the outer wall 233 thereof to accommodate the spinal nerve 55.

It should be pointed out that all or part of the protector means 11 may be constructed of a radio-opaque material for allowing the protector means 11 to be located by an X-ray or the like once it has been inserted in a patient for reasons apparent to those skilled in the art.

As thus constructed and inserted, the present invention provides a protector means 11 which prevents the development of postoperative adhesions and scar tissue on the dura 53 and spinal nerve 55 following intervertebral surgery to preclude the binding of the spinal nerve 55. The protector means 11 also permits easy access to the area again in case of unsatisfactory results.

Although the invention has been described and illustrated with respect to a preferred embodiment thereof, it is not to be so limited since changes and modifications may be made therein which are within the full intended scope of the invention.

I claim:

1. Protector means for use following intervertebral and intravertebral and intraspinal surgery at a surgical site on a patient to prevent postoperative adhesions from binding the patient's spinal nerves, said protector means comprising biocompatible shield means for providing an intervening barrier between portions of the patient's dura and spinal nerve roots and the patient's spinal canal structures adjacent the surgical site to prevent development of postoperative adhesions therebetween.

2. Protector means for preventing the development of postoperative adhesions between a patient's dura and spinal nerve roots and the patient's spinal canal structures adjacent a surgical site after the removal of a portion of the patient's intervertebral disc from the surgical site in which a portion of the patient's vertebra adjacent the disc is also removed from the surgical site, said protector means comprising:

a. biocompatible shield means for providing an intervening barrier between the patient's dura and spinal nerve roots and the patient's spinal canal structure adjacent the surgical site from which the portion of the disc was removed to prevent development of postoperative adhesions therebetween; and b. conduit means for covering a portion of the spinal nerve root adjacent the surgical site from which the portion of the disc was removed to prevent development of postoperative adhesions therebetween.

3. The protector means of claim 2 in which said shield means includes a semi-cylindrical body portion for extending around a portion of the dura adjacent the surgical site from which the portion of the disc was removed to prevent development of postoperative adhesions therebetween and includes a tongue portion for extending between the dura and the surgical site from which the portion of the vertebra was removed to obstruct passage therebetween.

4. The protector means of claim 3 in which said conduit means includes a tubular body portion for completely enveloping the portion of the spinal nerve adjacent the surgical site from which the portion of the disc was removed to prevent development of postoperative adhesions therebetween and includes a head portion for joining said body portion of said conduit means to said body portion of said shield means.

5. The protector means of claim 4 in which said body portion of said conduit means includes a longitudinal groove for allowing said body portion of said conduit means to be inserted around the spinal nerve.

6. The protector means of claim 5 in which said body portion of said conduit means includes a first longitudinal flange member adjacent the first side of said groove and includes a second longitudinal flange member adjacent the second side of said groove, said first and second longitudinal groove members being adjacent one another and being adapted to be joined to one another after said body portion of said conduit means is inserted around the spinal nerve.

7. The protector means of claim 2 in which is included roof means for covering the surgical site from which the portion of the vertebra was removed to obstruct passage therethrough and in which is included joining means for securely joining said roof means to said shield means.

8. The protector means of claim 7 in which is included filler means for occupying any vacant space in the spinal canal adjacent the surgical site from which the portion of the disc was removed to prevent development of postoperative adhesions therein.

9. Protector means for preventing the development of postoperative adhesions at a surgical site between a patient's dura and spinal nerves and the patient's spinal canal structure adjacent the surgical site after the removal of a portion of the patient's intervertebral disc from the surgical site in which a portion of the patient's spinal vertebra adjacent the disc is also removed from the surgical site, said protector means comprising:

a. biocompatible shield means for providing an intervening barrier between a portion of the patient's dura and the patient's spinal canal structures adjacent the surgical site from which the portion of the disc was removed, said shield means including a semi-cylindrical body portion for extending around a portion of the dura and nerve root adjacent the surgical site to prevent development of postoperative adhesions therebetween and including a tongue portion integrally joined to said body portion for extending between the dura and the surgical site from which the portion of the vertebra was removed to obstruct passage therebetween;

b. conduit means for covering a portion of the spinal nerve adjacent the surgical site from which the portion of the disc was removed, said conduit means including a tubular body portion for completely enveloping the portion of the spinal nerve adjacent the surgical site from which the portion of the disc was removed to prevent development of postoperative adhesions thereon and including a head portion integrally joined to said body portion for attachment to said body portion of said shield means to join said body portion of said conduit means to said body portion of said shield means;

c. roof means for covering the surgical site from which the portion of the vertebra was removed to obstruct passage therethrough;

d. joining means fixedly attached to said shield means and selectively attachable to said roof means for securely joining said roof means to said shield means; and e. filler means attached to said body portion of said shield means for occupying any vacant space in the spinal canal adjacent the surgical site from which the portion of the disc was removed to prevent development of postoperative adhesions therein.

10. The protector means of claim 9 in which said protector means is constructed of a flexible, biocompatible radio-opaque material.

11. The protector means of claim 1 in which said shield means includes a semi-cylindrical body portion for extending around a portion of the patient's dura adjacent the surgical site to prevent development of postoperative adhesions thereon and includes an offset portion for extending around a portion of the patient's spinal nerve adjacent the surgical site to prevent development of postoperative adhesions thereon.

12. The protector means of claim 11 in which said offset portion includes a plurality of grip members for holding the portion of the patient's spinal nerve to said offset portion.

13. The protector means of claim 3 in which said conduit means includes a first tubular body portion for completely enveloping the portion of the patient's spinal nerve adjacent the surgical site from which the portion of the disc was removed, a second tubular body portion for enveloping said first tubular body portion, and a plurality of flexible ribs for attaching said first tubular body portion inside said second tubular body portion while allowing said first tubular body portion a limited degree of movement relative to said second tubular body portion.

14. The protector means of claim 7 in which said roof means includes a plurality of finger members extending from said roof means to said shield means for occupying any vacant space between said roof means and said shield means to prevent development of postoperative adhesions therein.

15. Protector means for preventing the development of postoperative adhesions at a surgical site between a patient's dura and spinal nerves and the patient's spinal canal structure adjacent the surgical site after spinal surgery in which a portion of the patient's vertebra is removed from the surgical site, said protector means comprising biocompatible shield means for providing a barrier between the surgical site from which the portion of the patient's vertebra is removed and the patient's dura and spinal nerves.

16. The protector means of claim 15 in which said shield means includes a plurality of finger members for extending into the surgical site from which the portion of the vertebra is removed to occupy any vacant space therein to prevent development of postoperative adhesions thereon.

17. The protector means of claim 16 in which said shield means includes an arm portion having an outer end adapted to extend to adjacent the patient's skin to aid subsequent reentry to the patient's vertebrae.

18. The protector means of claim 17 in which said arm means includes a marker member positioned on said outer end thereof for aiding subsequent location of said arm portion.

19. Protector means for preventing the development of postoperative adhesions at a surgical site between a patient's dura and spinal nerves after the removal of a portion of the patient's intervertebral disc from the surgical site in which a portion of the patient's vertebra adjacent the disc is also removed from the surgical site, said protector means comprising:

a. biocompatible shield means for providing an intervening barrier between a portion of the patient's dura and the patient's spinal canal adjacent the surgical site from which the portion of the disc is removed to prevent development of postoperative adhesions therebetween and for covering a portion of the spinal nerve adjacent the surgical site from which the portion of the disc is removed to prevent development of postoperative adhesions therebetween; and b. stabilizing means for helping to stabilize said shield means adjacent the surgical site from which the portion of the disc is removed, said stabilizing means including a projecting member attached to said shield means for abutting portions of the patient's vertebra to stabilize said shield means.

20. The protector means of claim 19 in which is included fin means for helping to anchor said shield means adjacent the surgical site from which the portion of the disc is removed, said fin means including a flat, platelike member attached to said shield means for extending into the surgical site from which the portion of the disc is removed to anchor said shield means thereto; said flat, platelike member having a plurality of apertures therethrough for allowing adhesions and scar tissue to develop therethrough to firmly anchor said shield means thereto.

21. The protector means of claim 19 in which is included fastening means for fastening said shield means to the patient's vertebra adjacent the surgical site from which the portion of the disc is removed.

22. The protector means of claim 19 in which said shield means includes an offset portion for accomodating the patient's spinal nerve adjacent the surgical site from which the portion of the disc is removed.

23. The protector means of claim 19 in which said shield means includes an angularly extending inner wall for accommodating the patient's spinal nerve adjacent the rearward portion of the disc.

24. The protector means of claim 19 in which is included roof means for covering the surgical site from which the portion of the vertebra is removed, in which is included joining means for joining said shield means and said roof means, and in which said roof means and said joining means are adapted to allow said protector means to be anchored to the patient extra-durally.

25. The protector means of claim 3 in which said tongue portion of said shield means includes a backwardly curving portion for allowing the shield means to be anchored to the patient's spine.

26. The protector means of claim 25 in which said backwardly curving portion of said tongue portion of said shield means includes a plurality of apertures for allowing said shield means to be anchored to the patient's spine by sutures.

27. Protector means for use following intervertebral spinal surgery at a surgical site on a patient to prevent postoperative adhesions from binding the patient's spinal nerves, said protector means comprising biocompatible shield means for providing an intervening barrier between portions of the patient's dura and spinal nerves and the patient's spinal canal adjacent the surgical site to prevent development of postoperative adhesions therebetween, said shield means including a semi-cylindrical body portion for extending around a portion of the patient's dura adjacent the surgical site to prevent development of postoperative adhesions thereon and including an offset portion for extending around a portion of the patient's spinal nerve adjacent the surgical site to prevent development of postoperative adhesions therebetween.

28. The protector means of claim 11 in which said offset portion includes a plurality of grip members for holding the portion of the patient's spinal nerve to said offset portion.

* * * * *